United States Patent [19]

Brewer

[11] 4,152,412

[45] May 1, 1979

[54] MARKING VACCINE

[76] Inventor: John H. Brewer, 1402 Woodland Trail, Abilene, Tex. 79605

[21] Appl. No.: 848,408

[22] Filed: Nov. 4, 1977

Related U.S. Application Data

[63] Continuation-in-part of Ser. No. 673,117, Apr. 2, 1976, abandoned.

[51] Int. Cl.$^2$ .............. A61D 1/02; A61D 7/00; A61K 39/10
[52] U.S. Cl. .................................. 424/7; 128/316; 424/8; 424/9; 424/12; 424/88; 424/92; 424/93; 424/125
[58] Field of Search .............. 119/1; 128/316; 424/4, 424/7, 8, 9, 10, 11, 12, 13, 87–93, 125

[56] References Cited

U.S. PATENT DOCUMENTS

| | | | |
|---|---|---|---|
| 2,143,088 | 1/1939 | Rockwell | 424/125 |
| 2,496,270 | 2/1950 | Coler | 424/7 |
| 2,952,585 | 9/1960 | Heller | 424/87 |
| 3,096,249 | 7/1963 | Prigal | 424/7 |
| 3,097,141 | 7/1963 | Wilcox | 424/92 |
| 3,379,176 | 4/1968 | Propst | 128/316 X |
| 3,633,584 | 1/1972 | Farrell | 128/316 |

OTHER PUBLICATIONS

Birkhaug AJCP, vol. 17, 1947, pp. 751–754.
Rosenthal, JAMA, vol. 177, Aug. 12, 1961, pp. 196–198, 452–454.

*Primary Examiner*—Anna P. Fagelson
*Attorney, Agent, or Firm*—Marn & Jangarathis

[57] ABSTRACT

A vaccine, toxoid or like agent is administered to an animal by injecting the agent (usually intracutaneously) on a physiologically acceptable colored particle, preferably activated charcoal, which has a particle size whereby the colored particle remains at the point of injection to provide a visible mark which evidences administration of the vaccine or toxoid, and a repository of immunologically active material to serve as a booster.

14 Claims, No Drawings

MARKING VACCINE

This invention is a continuation-in-part of U.S. Applicaton Ser. No. 673,117, filed on Apr. 2, 1976 now abandoned.

This invention relates to the adminstration of vaccines, toxoids and like agents to animals.

This invention further relates to a new and improved vaccine. This invention further relates to an improved vaccine for immunization of animials against *Brucella abortus* and to the administration thereof.

Animals are currently immunized against a wide variety of diseases; however, in many cases, it is difficult to ascertain whether an animal has been immunized against a specific disease. Thus, for example, in the immunization of cattle against *Brucella abortus*, the cattle are injected with attenuated *Brucella abortus* organisms. In view of the fact that in many cases there are no clear records kept with respect to the immunization of specific cattle, in subsequent testing of the cattle to ascertain whether the cattle have *Brucella abortus*, a positive test may be obtained which is a result of the immunization, rather than the presence of the disease. Accordingly, there is a need for a positive manner of ascertaining whether an animal has been immunized against a specific disease, in that simplified routine current testing procedures generally do not distinguish between immunized and diseased animals.

In accordance with one aspect of the present invention, there is provided a method of administering vaccines, antigens, toxoids and like agents to an animal where the agent is injected, usually intracutaneously, in conjunction with a physiologically acceptable colored particle, with the particle having a particle size whereby the colored particle remains in the skin at the point of injection to thereby provide a visible mark which evidences administration of such agent. In this manner, immunization of the animal can be readily ascertained by ascertaining the presence of a colored particle. In accordance with the preferred embodiment, the agent is adsorbed on a colored adsorbent particle; i.e., a particle with a large internal surface area, whereby the particle containing adsorbed agent provides both a visible mark and a repository of the active material which can be released over a period of time.

The colored particle employed in the present invention may be any one of a wide variety of particles which is physiologically acceptable, and which will both retain the agent to be administered to the animal, prior to injection, and release the agent subsequent to injection. As representative examples of suitable particles, there may be mentioned: activated charcoal, ion exchange resins, adsorbent silica gel, alumina, and the like, with the activated charcoal being particularly preferred as a result of its large adsorbent properties; i.e., large internal surface area. If the finely divided solid adsorbent to be used does not have the desired color, it may be colored by treatment with a suitable dye or coloring e.g., malachite green or fluorescent material which can be detected. Naturally occurring colored particles such as yellow or red ochre, cobalt pigments, green chromium oxide, red iron oxide, Van Dyke brown, etc., may also be employed.

The colored particle employed in the present invention has a particle size such that the particle remains visible under the skin and is not immediately phagocytized. As a result, the particle usually has a particle size of at least 0.5 micron. The particle size, at the maximum, is limited to the ability to effectively administer the agent and particle to an animal by injection. As a result, the particle size is usually no greater than about 10 microns.

The colored adsorbent particle, and in particular activated charcoal, is preferably subjected to a vacuum prior to adsorbing the agent in order to remove any adsorbed gases and thereby increase the adsorption capacity thereof.

The agent which is administered to the animal in conjunction with the colored particle may be any one of a wide variety of agents currently administered to animals. Thus, for example, the agent may be a vaccine, including viral vaccines, such as administered for rabies, hog cholera, foot and mouth disease, influenza, distemper, New Castle disease, etc.; or a bacterial vaccine, such as administered for *Brucella abortus*, anthrax, erysipelothrix and the like; a toxoid, such as the detoxified toxin administered for tetanus; and the like. The selection of a particular agent to be administered in conjunction with the colored particle is deemed to be within the scope of those skilled in the art, and the specific agent employed forms no particular part of the present invention. Similarly, the amount of agent employed and the dosages administered are as known in the art and, accordingly, no details in this respect are deemed necessary for a complete understanding of the present invention.

The colored particle is preferably a porous adsorbent and, consequently, the agent is adsorbed on or in the adsorbent prior to injection thereof into the animal. The agent is adsorbed on the adsorbent by any one of a wide variety of procedures known in the art. A convenient means of producing the colored particle with the adsorbed agent is by mixing the agent, in suspension or solution, with a small amount of the adsorbent under conditions of time, temperature, pH and the like to permit adsorption of the agent on the colored particle. The solid particle, containing adsorbed agent, may be separated from the solution for use in a suitable vehicle for administration thereof by injection. The adsorption of the agent on a colored particle is deemed to be within the scope of those skilled in the art from the teachings herein.

In accordance with the present invention, the agent to be administered may be employed as a whole organism or may be lysed, prior to adsorption thereof. Similarly, in accordance with the present invention, the dosage to be administered to the animal may include the agent in both adsorbed and non-adsorbed form. In accordance with the particularly preferred aspect of the present invention, the dosage includes the lysed agent adsorbed on the colored particle. In some cases, the whole organism in unadsorbed form is also injected with the whole organism providing an immediate response and the adsorbed agent being slowly released as a booster. In some cases, in order to produce the proper immunity, it may be necessary to inject the usual vaccine and adsorbed vaccine intramuscularly or subcutaneously in conjunction with the intradermal injection.

In employing the present invention, a code may be provided in order to ascertain whether an animal has been immunized against a specific disease. Thus, for example, a different colored particle may be employed in conjunction with each agent, whereby examination of an animal to ascertain the presence of a particular colored particle will indicate whether the animal has been immunized against a specific disease. Alternatively, a code can be provided by which different agents are injected at different specific portions of the animal body, whereby the presence of a colored particle in the skin of the animal at a particular portion of the animal body will be indicative of the fact that the animal has been immunized against a specific disease. These and other codes should be readily apparent to those skilled in the art from the teachings herein.

In accordance with the present invention, it has been found that a lysed vaccine which is adsorbed on a colored adsorbent particle (large internal surface area) provides both a visible mark which evidences use of the vaccine and an increased immunogenic potency. In cases where the vaccine has a small cell size it may not be necessary to lyse the vaccine prior to adsorption in order to maximize the immunogenic potential. Although activated charcoal is the preferred colored adsorbent particle, it is to be understood that other colored adsorbent particles may be employed.

The invention will be further described with respect to the following example; however, the invention is not to be limited thereby.

EXAMPLE I

Live, attenuated *Brucella abortus* strain 19 vaccine was treated by four separate procedures and adsorbed onto activated charcoal. One method employed the standard vaccine, the second employed the standard vaccine which had been heat-killed at 60° C. for two hours, and the third employed the standard vaccine which had been lysed for 6 minutes at 200 watts by a Model W-200-R Heat Systems Ultrasonics sonicator cell disruptor and the fourth employed equal amounts of the standard and lysed vaccines. These were adsorbed separately onto activated charcoal (particle size range 0.5–5 microns) by allowing them to incubate in contact overnight on a shaker at 3° C. These were suspended in the standard vaccine suspension fluid. The activated charcoal which we employ is an amorphous mass with unbelievable surface area, which had been subjected to vacuum overnight. Under the electron microscope these particles look like a sponge (30,000×). Dosage for injection into rabbits was determined by body weight ratios, and intracutaneous injection procedures were used. Dosage was standardized to give an equivalent dose for each method. The charcoal was clearly visible throughout the duration of the experiment, and antibody titers were demonstrated. In principle this same technique would be used for other immunological agents. In each procedure, including unadsorbed strain 19, the dosage was $6.0 \times 10^7$ organisms with the charcoal concentration, when present, being 0.1%, weight per volume. The standard dose for strain 19 vaccination of 3 month old calves is a total of $6.0 \times 10^{10}$ organisms. The anti-brucellosis titers in the rabbits (3 lbs.) was as follows:

(1) Strain 19—No charcoal—Maximum titer of 800 in 15 days decreasing to 200 in 45 days.

(2) Strain 19—Adsorbed onto charcoal—Maximum titer of 800 in 20 days decreasing to 200 in 52 days.

(3) Lysed strain 19—Adsorbed onto charcoal—Maximum titer of 2400 in 12 days decreasing to a low of 600 in 40 days.

(4) Adsorbed lysed + adsorbed standard—Maximum titer of 1600 in 12 days decreasing to a low of 800 in 50 days.

(5) Adsorbed heat-killed vaccine—Maximum titer of 200 in 12 days, decreasing to a low of 25 in 52 days.

(6) Charcoal only—Negative serological tests.

EXAMPLE II

In each procedure, guinea pigs were vaccinated with 0.25 ml. of a vaccine containing $6.0 \times 10^7$ cells or lysed cells (charcoal concentration in activated charcoal adsorbed vaccine was 0.1% weight per volume), held for 6 weeks, and challenged with $10^5$ cells of the pathogenic *B. abortus* strain 2308 (this is the standard challenge dose for calves). Ten days after challenge the animals were sacraficed, and the spleen and abdominal lymph nodes cultured to determine presence or absence of infection. The results of these protection studies are as follows:

| VACCINE | TOTAL # OF ANIMALS VACCINATED | # INFECTED (%) | # NOT INFECTED (%) |
|---|---|---|---|
| Standard Strain 19 | 51 | 31 (60.8) | 20 (39.2) |
| Lysed, charcoal adsorbed Strain 19 | 107 | 22 (20.6) | 85 (79.4) |
| Unvaccinated controls | 45 | 43 (95.6) | 2 (4.4) |
| Unchallenged controls | 8 | 0 (0.0) | 8 (100.0) |

The present invention is particularly advantageous in that it can be readily ascertained whether an animal has been immunized against a specific disease. In addition, the marking of the animal is effected simultaneously with the immunization, thereby eliminating necessity for separate records and/or steps for effecting proper tagging of the animal.

As a further advantage, the adsorption of the agent on the colored particles provides for release of the agent over a period of time, thereby providing a repository of immunologically active material to serve as a booster. As a result of the ability to obtain sustained release by injection of the vaccine adsorbed on the colored particle, the vaccine can be adsorbed in either attenuated or killed form.

The use of vaccine adsorbed on the solid particles, and in particular the lysed vaccine, increases the immunogenic potency of vaccines, as evidenced by increased antibody titers and an increase in the level of protection.

The use of lysed vaccine for *Brucella abortus* adsorbed on a solid particle as hereinabove described, and in particular adsorbed on charcoal, is an improvement over the standard vaccine in that the vaccine provides for marking of the animal, and does not result in infection, thereby eliminating the problem of possible sterility in bulls and the potential health hazard to man. The vaccine also provides higher titers and increased protection.

Furthermore, the vaccine has increased shelf life in that it is non-viable.

Numerous modifications and variations of the present invention are possible in light of the above teachings and, therefore, within the scope of the appended claims, the invention may be practised otherwise than as particularly described.

What is claimed is:

1. In the method of administering vaccines, antigens, toxoids or other immunizing agents to an animal, the improvement comprising:
    injecting an effective amount of the agent into the skin of the animal in conjunction with a physiologically acceptable colored particle having a particle size whereby the colored particle remains at the point of injection to provide a visible mark which evidences administration of said agent.

2. The method of claim 1 wherein the agent is adsorbed on said colored particle.

3. The method of claim 2 wherein the colored particle is activated charcoal.

4. The method of claim 3 wherein the colored particle has a particle size of at least 0.5 micron.

5. The method of claim 4 wherein the agent is in lysed form.

6. The method of claim 5 wherein the agent is administered as a combination of the whole organism and the agent in lysed form adsorbed on said activated charcoal.

7. The method of claim 4 wherein the agent is *Brucella abortus* vaccine.

8. The method of claim 4 wherein the agent is rabies vaccine.

9. The method of claim 4 wherein the agent is killed vaccine.

10. In a method of vaccinating an animal against *Brucella abortus*, the improvement comprising: injecting into the skin an effective amount of *Brucella abortus* vaccine adsorbed on a physiologically acceptable colored particle having a particle size whereby the colored particle remains at the point of injection to provide a visible mark which evidences administration of said vaccine.

11. The method of claim 10 wherein the vaccine is in lysed form adsorbed on activated charcoal having a particle size of at least 0.5 micron.

12. A composition for vaccinating an animal, comprising:

*Brucella Abortus* vaccine in lysed form, adsorbed on colored adsorbent particles, said vaccine being adsorbed on colored adsorbent particles having a particle size of at least 0.5 micron to provide upon injection a visible mark and a repository of the vaccine for release over a period of time.

13. The composition of claim 12 wherein the adsorbent particles are activated charcoal.

14. The composition of claim 13 wherein the activated charcoal was subjected to vacuum to remove adsorbed gases prior to adsorption of the vaccine.

* * * * *